United States Patent
Lee et al.

(10) Patent No.: US 11,091,422 B2
(45) Date of Patent: *Aug. 17, 2021

(54) METHOD FOR REMOVING MONOHYDRIC ALCOHOL FROM ESTERIFICATION AND METHOD FOR PREPARING ESTER COMPOSITION COMPRISING SAME

(71) Applicant: LG CHEM, LTD., Seoul (KR)

(72) Inventors: Ha Na Lee, Daejeon (KR); Sung Kyu Lee, Daejeon (KR); Joon Ho Shin, Daejeon (KR); Hyoung Jun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/628,239

(22) PCT Filed: Sep. 5, 2018

(86) PCT No.: PCT/KR2018/010381
§ 371 (c)(1),
(2) Date: Jan. 2, 2020

(87) PCT Pub. No.: WO2019/050280
PCT Pub. Date: Mar. 14, 2019

(65) Prior Publication Data
US 2021/0040026 A1   Feb. 11, 2021

(30) Foreign Application Priority Data

Sep. 7, 2017 (KR) .................. 10-2017-0114623

(51) Int. Cl.
*C07C 67/08* (2006.01)
*C07C 67/54* (2006.01)
*C07C 69/82* (2006.01)

(52) U.S. Cl.
CPC .............. *C07C 67/08* (2013.01); *C07C 67/54* (2013.01); *C07C 69/82* (2013.01)

(58) Field of Classification Search
CPC .......... C07C 67/08; C07C 67/54; C07C 69/82
See application file for complete search history.

(56) References Cited

U.S. PATENT DOCUMENTS

| | | | |
|---|---|---|---|
| 3,681,434 A * | 8/1972 | Neely ...................... | C07C 69/80 560/98 |
| 4,314,947 A * | 2/1982 | Hohenschutz .......... | C07C 67/08 202/158 |
| 6,174,970 B1 | 1/2001 | Braune | |
| 6,300,467 B1 | 10/2001 | Auer et al. | |
| 8,217,191 B2 | 7/2012 | Aiken | |
| 2004/0106813 A1 | 6/2004 | Moritz et al. | |
| 2005/0163679 A1 | 7/2005 | Schulz Van Endert et al. | |
| 2006/0178524 A1 | 8/2006 | Zuber et al. | |
| 2006/0199971 A1 | 9/2006 | Moritz et al. | |
| 2007/0066790 A1 | 3/2007 | Schulz Van Endert et al. | |
| 2010/0137631 A1 | 6/2010 | De Munck et al. | |

FOREIGN PATENT DOCUMENTS

| | | |
|---|---|---|
| EP | 2851393 A1 | 3/2015 |
| JP | 2001172235 | 6/2001 |
| JP | 2014097939 | 5/2014 |
| KR | 10-19990087569 | 12/1999 |
| KR | 10-20010013913 | 2/2001 |
| KR | 10-20040047563 | 6/2004 |
| KR | 10-20050002807 | 1/2005 |
| KR | 10-20050107449 | 11/2005 |
| KR | 10-20060090764 | 8/2006 |
| KR | 10-0830278 | 5/2008 |
| KR | 10-20090130042 | 12/2009 |
| KR | 10-20130051453 | 5/2013 |
| KR | 10-1354141 | 1/2014 |
| WO | 1997-032915 | 9/1997 |
| WO | 2004076513 | 9/2004 |
| WO | 2011-131609 | 10/2011 |
| WO | 2014-182083 | 11/2014 |

OTHER PUBLICATIONS

Rahman et al., "The plasticizer market: an assessment of traditional plasticizers and research trends to meet new challenges," Progress in Polymer Science 29:1223-1248 (2004).

Janjua et al., "Systemic Uptake of Diethyl Phthalate, Dibutyl Phthalate, and Butyl Paraben Following Whole-Body Topical Application and Reproductive and Thyroid Hormone Levels in Humans," Environmental Science and Technology 41:5564-5570 (2007).

Melero et al., "Heterogeneous acid catalysts for biodiesel production: current status and future challenges," Green Chemistry 11:1285-1308 (2009).

* cited by examiner

Primary Examiner — Yevgeny Valenrod
Assistant Examiner — Blaine G Doletski
(74) Attorney, Agent, or Firm — Dentons US LLP

(57) ABSTRACT

Provided is a monohydric alcohol removal method in esterification, the method including a step of reacting a carbonyl-based compound having one or more functional groups selected from the group consisting of carboxyl, ester, and acid anhydride groups with a monohydric alcohol in an esterification reactor including a liquid phase outlet line connected to a liquid phase section in the reactor, and a step of separating in a gas-liquid separation column to remove the monohydric alcohol, wherein the inflow of a liquid phase stream into the gas-liquid separation column starts at the time point between 10% and 70% of the total time required for the gas-liquid separation.

7 Claims, 1 Drawing Sheet

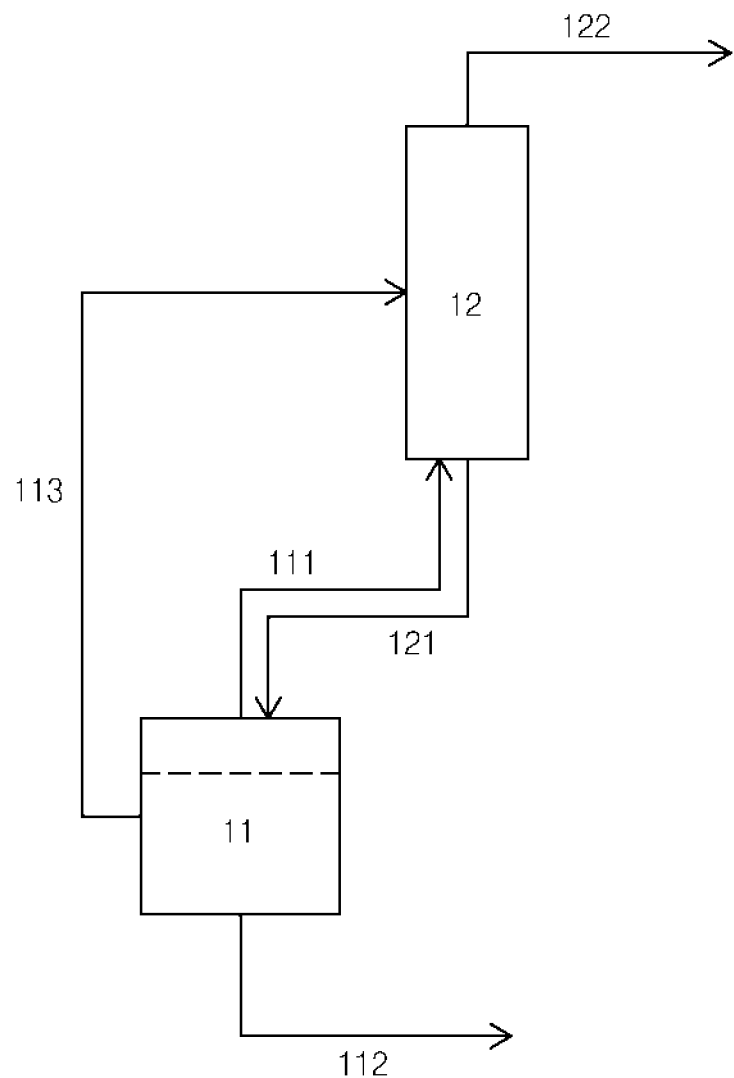

METHOD FOR REMOVING MONOHYDRIC ALCOHOL FROM ESTERIFICATION AND METHOD FOR PREPARING ESTER COMPOSITION COMPRISING SAME

CROSS-REFERENCE TO RELATED APPLICATIONS

This application is a National Stage Application of International Application No. PCT/KR2018/010381 filed on Sep. 5, 2018, which claims priority to and the benefit of Korean Patent. Application No. 10-2017-0114623, filed on Sep. 7, 2017, the entire contents of which are incorporated herein by reference.

Technical Field

The present invention relates to a method for removing monohydric alcohol from esterification using a gas-liquid separation system and a method for preparing an ester composition using the same.

Background Art

A phthalate-based plasticizer accounts for 92% of the global plasticizer market (see Mustafizur Rahman. and Christopher S. Brazel, Progress in Polymer Science 2004, 29, 1223-1248, "The plasticizer market: an assessment of traditional plasticizers and research trends to meet new challenges"). It is an additive used for imparting flexibility, durability and cold resistance mainly to polyvinyl chloride (hereinafter referred to as PVC) and lowering the viscosity during melting to improve processability. It is added in various amounts to PVC and widely used in various applications from rigid products such as rigid pipes to soft products which can be used, for example, as food packaging materials, blood bags, flooring materials, etc. due to its soft and good flexibility. Likewise, the plasticizer is more closely related to real life than any other material, so direct contact with the human body may not be avoidable.

However, despite the compatibility of the phthalate-based plasticizer with PVC and its excellent capability to impart flexibility, it has been argued recently about harmfulness of the PVC product containing the phthalate-based plasticizer that the phthalate-based plasticizer can leak out of the PVC product when used in real life, and act as a presumed endocrine disrupting (environmental hormone) substance and a carcinogen of the level of heavy metals (see N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570). Especially, since the report about the leakage of di-(2-ethyl hexyl) phthalate (DEHP), which was the most used phthalate-based plasticizer in the US in the 1960s, out of the PVC product, the interest in environmental hormones have been added in the 1990s and global environmental regulations as well as various studies on hazards of the phthalate-based plasticizer to human have been started.

Therefore, in order to cope with environmental hormone problems and environmental regulations due to the leakage of the phthalate-based plasticizer, many researchers have been conducting research to develop a new, alternative, non-phthalate-based plasticizer which is free of phthalic anhydride used in the production of phthalate-based plasticizers or a leakage inhibition technology which can inhibit the leakage of the phthalate-based plasticizer to greatly reduce the hazards to human and be in accordance with environmental standards.

Meanwhile, as a non-phthalate-based plasticizer, a terephthalate-based plasticizer has been getting the spotlight, because it is equivalent to the phthalate-based plasticizer in terms of physical properties, but is free of environmental issues. A variety of terephthalate-based plasticizers have been developed and research on the development of a terephthalate-based plasticizer having excellent physical properties, as well as researches on facilities for preparing such the terephthalate-based plasticizer have been actively conducted. In terms of process design, more efficient, economical and simple process design has been required.

PRIOR ART DOCUMENTS

Patent Document (Patent Document 1) Korean Patent No. 10-1354141

Non-Patent Documents (Non-patent Document 1) Mustafizur Rahman and Christopher S. Brazel "The plasticizer market: an assessment of traditional plasticizers and research trends to meet new challenges" Progress in Polymer Science 2004, 29, 1223-1248

(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570.

DISCLOSURE OF THE INVENTION

Technical Problem

The present invention relates to a removal method capable of effectively removing unreacted alcohol in a reactor, and an aspect of the present invention provides a monohydric alcohol removal method in an esterification process, which is capable of removing unreacted alcohol in an esterification reactor with high efficiency in a short time.

Technical Solution

According to an aspect of the present invention, there is provided a monohydric alcohol removal method in esterification, the method comprising, a step of reacting a carbonyl-based compound having one or more functional groups selected from the group consisting of carboxyl, ester, and acid anhydride groups with a monohydric alcohol in an esterification reactor comprising a reaction space having a liquid phase section and a gas phase section, a gas phase outlet line located at the upper part of the reaction space and connected to the gas phase section in the reactor, and a liquid phase outlet line located at the side part of the reaction space and connected to the liquid phase section in the reactor; and a step of separating a gas phase stream containing the monohydric alcohol from the gas phase outlet line and a liquid phase stream containing the monohydric alcohol from the liquid phase outlet line in a gas-liquid separation column so as to remove the monohydric alcohol, wherein the inflow of the liquid phase stream into the gas-liquid separation column starts at the time point between 10% and 70% of the total time required for the gas-liquid separation.

According to another aspect of the present invention, there is provided an ester composition preparation method, comprising the monohydric alcohol removal method in esterification as described above, wherein the esterification is direct esterification, and the method further comprises a step of additionally putting alcohol for trans-esterification into the esterification reactor so as to perform trans-esterification after the monohydric alcohol removal step, and the carbonyl-based compound is one in which two or more of carboxyl, ester, or acid anhydride groups are bound.

Advantageous Effects

According to the present invention, unreacted alcohol can be removed in the esterification reactor to a desired level within a short time. Therefore, when the removal method according to the present invention is applied to the direct esterification, excellent conversion rate can be obtained even by direct esterification, followed by trans-esterification in the same reactor. Consequently, the direct esterification process and the trans-esterification process can be integrated, and economical efficiency can also be obtained due to factory equipment reduction, etc.

BRIEF DESCRIPTION OF THE DRAWINGS

The FIGURE is a process flow chart illustrating an example of a process of removing monohydric alcohol according to a monohydric alcohol removal method in the esterification of the present invention.

MODE FOR CARRYING OUT THE INVENTION

Hereinafter, the present invention will be described in more detail to help an understanding of the present invention.

The terms or words used in the description of the present invention and claims shall not be interpreted as being limited to ordinary or dictionary meanings and the terms or words should be interpreted as meanings and concepts consistent with the technical idea of the present invention, based on the principle that an inventor can properly define the concept of a term to explain his own invention in the best way.

According to an aspect of the present invention, there is provided a monohydric alcohol removal method in esterification, the method comprising, a step of reacting a carbonyl-based compound having one or more functional groups selected from the group consisting of carboxyl, ester, and acid anhydride groups with a monohydric alcohol in an esterification reactor comprising a reaction space having a liquid phase section and a gas phase section, a gas phase outlet line located at the upper part of the reaction space and connected to the gas phase section in the reactor, and a liquid phase outlet line located at the side part of the reaction space and connected to the liquid phase section in the reactor; and a step of separating a gas phase stream containing the monohydric alcohol from the gas phase outlet line and a liquid phase stream containing the monohydric alcohol from the liquid phase outlet line in a gas-liquid separation column so as to remove the monohydric alcohol, wherein the inflow of the liquid phase stream into the gas-liquid separation column starts at the time point between 10% and 70% of the total time required for the gas-liquid separation.

The gas-liquid separation system used for the monohydric alcohol removal method can include the esterification reactor including the inner reaction space in which the reaction is carried out, the gas phase outlet line, and a product line; and the gas-liquid separation column having a gas-liquid separation space, a lower recovery line, and an upper outflow line provided therewith, and can include the liquid phase outlet line which is connected from the liquid phase section in the esterification reactor to the side part of the gas-liquid separation column.

Specifically, the esterification reactor can include the reaction space, in which esterification is carried out and which has the liquid phase section and the gas phase section, the gas phase outlet line located at the upper part of the reaction space and connected to the gas phase section in the reactor, and the product line located at the lower part of the reaction space and connected to the liquid phase section in the reactor.

The gas-liquid separation column can have the gas-liquid separation space, into which the gas phase stream, containing gasified reaction products and a gas phase low boiling point mixture from the esterification reactor, flows through the gas phase outlet line of the reactor and in which the gas-liquid separation is carried out, the lower recovery line, in which liquefied reaction products are recovered to the esterification reactor, and the upper outflow line, in which the gas phase low boiling point mixture is removed and flowed out, provided therewith.

In addition, the liquid phase outlet line can be located at the side part of the esterification reactor and connected to the liquid phase section so as to flow the liquid phase stream out and connected to the side part at one half of the gas-phase separation column or higher in the height direction of the column so as to provide the liquid phase stream to the column.

Meanwhile, in the case of the esterification process, in particular, in the process for preparing an esterified composition through the trans-esterification of an ester compound, the direct esterification process and the trans-esterification process are generally carried out separately. In order for the direct esterification process and the trans-esterification process to be integrated into one process, the integration of reactors must be preceded.

However, when the direct esterification and the trans-esterification are carried out in one reactor, following the direct esterification, the trans-esterification proceeds using the ester compound, which is the product of the direct esterification. Then, if the low boiling point mixture containing unreacted alcohol in the direct esterification remains in excess of a certain amount, there are problems that the forward reaction of the trans-esterification does not progress smoothly, and consequently, that the conversion rate of the trans-esterification can be considerably deteriorated.

Accordingly, it is essential for the integration of the reactions to remove the low boiling point mixture containing unreacted monohydric alcohol after the direct esterification to a certain amount or less.

In this regard, in the conventional esterification process, the low boiling point mixture, such as unreacted monohydric alcohol and the like, was removed by transferring gas phase substances to the gas-liquid separation column through reduction in pressure in order to remove the low boiling point mixture containing unreacted monohydric alcohol in the esterification reactor so as to perform the gas-liquid separation. However, the gas-liquid separation through the reduction in pressure may not reduce the concentration of the unreacted alcohol in the reactor to a desired level due to poor efficiency caused by small mass transfer area. Even if it can reduce the concentration, there is a problem that the entire process is delayed due to its very low speed.

However, in the case of applying the monohydric alcohol removal method according to an aspect of the present invention, the esterification reactor has the liquid phase outlet line provided therewith and thus, in addition to the stream flowed into the gas-liquid separation column as the gas stream through the reduction in pressure, the liquid phase stream flows together into the liquid phase outlet line which allows the liquid phase itself in the reactor to flow into the gas-liquid separation column. Therefore, the efficiency of the gas-liquid separation can be maximized and the time for which the unreacted monohydric alcohol is removed can be greatly reduced, and the content of the remaining unreacted monohydric alcohol in the reactor can be reduced to a minute amount. When such monohydric alcohol removal method is applied to the direct esterification, it is possible to integrate the process with the trans-esterification as described above, and the product of the trans-esterification can be obtained at a high yield.

According to an aspect of the present invention, the monohydric alcohol removal method in the esterification can be roughly classified into the esterification step and the monohydric alcohol removal step. The esterification step is reacting the carbonyl compound having one or more functional groups selected from the group consisting of carboxyl, ester, and acid anhydride groups with the monohydric alcohol in the above described esterification reactor, and the monohydric alcohol removal step is flowing the gas phase stream and the liquid phase stream from the esterification reactor to the above described gas-liquid separation column so as to perform the gas-liquid separation and remove the monohydric alcohol.

In the step of performing the esterification, general esterification can be performed, and the conditions of the esterification can be known reaction conditions.

In addition, the step of removing the monohydric alcohol can be flowing the gas phase stream through the gas phase outlet line of the esterification reactor and the liquid phase stream through the liquid phase outlet line of the esterification reactor into the gas-liquid separation column and removing the monohydric alcohol in the gas-liquid separation column. The monohydric alcohol can be gasified during the reaction, so as to be included in the gas phase stream, and can be intactly in liquid form, so as to be included in the liquid phase stream. That is, both the liquid phase stream and the gas phase stream can contain the monohydric alcohol and flow into the gas-liquid separation column, and the conditions applied to the gas-liquid separation can be all the commonly used conditions.

However, in the monohydric alcohol removal method, it is necessary to control the time point when the liquid phase stream is transferred to the gas-liquid separation column in the entire separation process. That is, control of the flow of the liquid phase stream through the liquid phase outlet line to the gas-liquid separation column after the elapse of about 10% to 70%, preferably 30% to 70%, 35% to 65%, more preferably 40% to 60%, optimally 45% to 58% of the total time required for the gas-liquid separation process can be required. If the liquid phase stream is transferred to the gas-liquid separation column from the time point when the gas-liquid separation starts or before 10% of the total time elapsed, the monohydric alcohol can be removed to a certain content. However, there can be no improvement in the removal speed and there can be no big difference from those into which the liquid phase outlet line is not introduced.

That is, if the time point when the liquid phase stream flows from the reactor to the gas-liquid separation column is controlled, the gas-liquid separation efficiency can be maximized, and the time point can be when about 10 to 70% of the time required for the entire separation process lapsed.

Generally, the time required for the gas-liquid separation process, that is, the removal of the monohydric alcohol can be about 80 minutes to 140 minutes. However, the time can be varied depending on the volume of the reactor, the separation capacity of the gas-liquid separation column, and the like and the time required for the entire separation process can be decreased due to the presence of additional separation processes. Therefore, the total time required for the separation process is not particularly limited.

Furthermore, the greater the flow of the liquid stream, the efficiency of separation can increase. It can be advantageous that the flow is about 25% or more of the total amount of reaction products in liquid phase in the reactor. However, as the flow of the liquid phase stream increases, the efficiency of the gas-liquid separation does not increase proportionally, but the efficiency increase can be remarkably larger than the flow increment.

In addition to the unreacted alcohol, an example of the components contained in the low boiling point mixture can be moisture, and the removal of moisture can also be an important factor in the esterification. However, the removal of moisture plays a more important role during the esterification and thus, in the step of removing the monohydric alcohol after completion of the reaction, it can be common that the moisture is removed along with the monohydric alcohol.

The gas-liquid separation space of the gas-liquid separation column can be of a tray type, a packed type, or a mixed type thereof, and thus, which can be referred to as a tray column, a packed column, or a tray/packed mixed column. The gas-liquid separation column in the gas-liquid separation system according to an aspect of the present invention can be appropriately adjusted depending on components contained in the low boiling point mixture to be removed and the contents thereof.

The monohydric alcohol which is the raw material in the esterification can have an alkyl group having 2 to 20 carbon atoms. In addition, the carbonyl compound can be any compound having one or more ester, carboxy, or acid anhydride groups as a functional group and examples include acetic acid and esters or acid anhydrides thereof, phthalic acid and esters or acid anhydrides thereof, isophthalic acid and esters or acid anhydrides thereof, terephthalic acid and esters or acid anhydrides thereof, citric acid and esters or acid anhydrides thereof, succinic acid and esters or acid anhydrides thereof, trimellitic acid and esters or acid anhydrides thereof, benzoic acid and esters or acid anhydrides thereof, and propionic acid, butyric acid, or pentanoic acid, in addition to the acetic acid, and esters derived from natural oils or epoxidized oils thereof. That is, the monohydric alcohol removal method according to an aspect of the present invention can be applied without limitation to the process in which the reaction between compounds capable of esterification is performed.

According to an aspect of the present invention, there is provided an ester composition preparation method including the monohydric alcohol removal method described above.

Specifically, the method includes: a step of reacting a carbonyl-based compound having one or more functional groups selected from the group consisting of carboxyl, ester, and acid anhydride groups with a monohydric alcohol in the esterification reactor; a step of flowing the gas phase stream and the liquid phase stream, containing the monohydric alcohol, from the esterification reactor to the gas-liquid separation column so as to remove the monohydric alcohol; and a step of putting alcohol having different number of carbon atoms from the monohydric alcohol into the esterification reactor so as to perform the trans-esterification.

As described above, when the monohydric alcohol removal method according to an aspect of the present invention is applied to the direct esterification, trans-esterification can be carried out in the same reactor, and through this, the integration of the reaction equipment can be accomplished. Therefore, advantages in various aspects such as economic feasibility, processability, and the like can be attained.

Hereinafter, one example of the gas-liquid separation system applied to the monohydric alcohol removal method according to an aspect of the present invention will be described in detail with reference to the accompanying drawing.

The FIGURE is a process flow chart illustrating an example of a gas-liquid separation system. Referring to The FIGURE, the esterification reactor 11 having an inner space in which direct esterification is carried out, a liquid phase section, and a gas phase section provided therewith, has the gas phase outlet line 111 located at the upper part of the reaction space and connected to the gas phase section so as to flow out the gas stream, and the product line 112 located at the lower part of the reaction space and connected to the liquid phase section so as to flow out products provided therewith.

The gas phase stream which flows out through the gas phase outlet line 111 can be connected to the lower part of the gas-liquid separation column 12. The gas-liquid separation column 12 has a gas-liquid separation space in which the gas-liquid separation of the gas phase stream flowed in is carried out and the gas-liquid separation column 12 can have, at the upper part, an upper outflow line 122, in which a low boiling point compound including unreacted alcohol is removed, and at the lower part, a lower recovery line 121, in which re-liquefied reaction products through the gas-liquid separation are recovered, provided therewith.

In addition, the gas-liquid separation column 12 can have the liquid phase outlet line 113, which is connected from the liquid phase section in the esterification reactor 11 to the side part of the gas-liquid separation column 12, provided therewith, in order to be connected with the liquid phase section in the esterification reactor 11 to flow out the liquid phase stream and to flow the outflowed liquid phase stream into the gas-liquid separation column 12.

The liquid phase outlet line 113 can be located at the side part of the esterification reactor 11 or can be located together with the product line 112 at the lower part of the esterification reactor 11. That is, the position of the liquid phase outlet line 113 is not particularly limited so long as the liquid phase outlet line 113 is connected to the liquid phase section in the reactor 11. In addition, it can be preferable that the part to be introduced into the gas-liquid separation column 12 is also located at the side part of the gas-liquid separation column 12, and it can be preferable that the part is introduced into the side part at one half of the column or higher in the height direction of the column. However, it is also possible to design the liquid phase outlet line 113 so as to introduce into the upper part of the gas-liquid separation column 12.

Furthermore, in the case of the gas-phase stream flowing through the gas-phase outlet line 111, it can flow through reduction in the pressure of the esterification reactor 11, but in the case of the liquid phase stream, a power source such as a pump (not shown) can be provided on the liquid outlet line 113 in order to transfer the liquid phase stream to above a certain height of the gas-liquid separation column 12.

EXAMPLES

Hereinafter, the present invention will be described in more detail by examples. However, the following examples are for illustrative purposes only and the scope of the present invention is not limited thereto.

In the following examples and comparative examples, the method for removing the monohydric alcohol in esterification of the present invention was simulated by using the commercial process simulation program, ASPEN PLUS and the gas-liquid separation was conducted while decreasing pressure from atmospheric pressure to 80 torr for 120 minutes.

Example 1

Terephthalic acid (5.5 T/hr) and 2-ethyl hexanol (13.5 T/hr) were introduced into the esterification reactor (11) as raw materials for the reaction to conduct the direct esterification. After completion of the reaction, the liquid phase stream was flowed into the gas-liquid separation column through the liquid phase outlet line 54 minutes after the start of the separation, when about 45% of the total separation process time elapsed. The gas-liquid separation was performed for a total of 120 minutes by controlling total influx of the liquid phase stream through the liquid phase outlet line to 100% of the total amount of the reaction products in the liquid phase in the reactor.

Example 2

The gas-liquid separation was performed in the same manner as in Example 1 except that the liquid phase stream was flowed into the gas-liquid separation column through the liquid phase outlet line from about 70 minutes after the start of separation, when about 58% of the total separation process time elapsed.

Example 3

The gas-liquid separation was performed in the same manner as in Example 1 except that the liquid phase stream was flowed into the gas-liquid separation column through the liquid phase outlet line from about 15 minutes after the start of separation, when about 12.5% of the total separation process time elapsed.

Example 4

The gas-liquid separation was performed in the same manner as in Example 1, except that it was performed for a total of 120 minutes by controlling total influx of the liquid phase stream through the liquid phase outlet line to 25 weight % of the total amount of the reaction products in the liquid phase in the reactor.

Example 5

The gas-liquid separation was performed in the same manner as in Example 4 except that the liquid phase stream was flowed into the gas-liquid separation column through the liquid phase outlet line from 54 minutes after the start of separation, when about 45% of the total separation process time elapsed.

Example 6

The gas-liquid separation was performed in the same manner as in Example 4 except that the liquid phase stream was flowed into the gas-liquid separation column through the liquid phase outlet line from 15 minutes after the start of separation, when about 12.5% of the total separation process time elapsed.

Comparative Example 1

The gas-liquid separation was performed without applying the liquid phase outlet line, and the same conditions of the esterification and the gas-liquid separation as in Example 1 were applied.

Comparative Example 2

The gas-liquid separation was performed in the same manner as in Example 1 except that the liquid phase stream was flowed into the gas-liquid separation column through the liquid phase outlet line from the starting time point of separation.

Comparative Example 3

The gas-liquid separation was performed in the same manner as in Example 4 except that the liquid phase stream was flowed into the gas-liquid separation column through the liquid phase outlet line from the starting time point of separation.

Experimental Example 1

In the gas-liquid separation in Examples 1 to 6 and Comparative examples 1 to 3, the time required for separation until the content of 2-ethyl hexanol in the esterification reactor is 2 weight % or less, and the reduction rate of the time required for separation were calculated and the results were shown in Tables 1 and 2 below.

TABLE 1

|  | The ratio of liquid phase stream[1] (weight %) | Starting time point of separation | Time required for separation (min) | Reduction rate of time required for separation (%) |
| --- | --- | --- | --- | --- |
| Example 1 | 100 | 54 min, 45% | 90.0 | 25.0 |
| Example 2 | 100 | 70 min, 58% | 99.6 | 17.0 |
| Example 3 | 100 | 15 min, 12.5% | 105.6 | 12.0 |
| Comparative example 1 | 0 | — | 120.0 | 0.0 |
| Comparative example 2 | 100 | immediately | 112.8 | 6.0 |

TABLE 2

|  | The ratio of liquid phase stream[1] (weight %) | Starting time point of separation | Time required for separation (min) | Reduction rate of time required for separation (%) |
| --- | --- | --- | --- | --- |
| Example 4 | 25 | 54 min, 45% | 105.0 | 12.5 |
| Example 5 | 25 | 70 min, 58% | 110.4 | 8.0 |
| Example 6 | 25 | 15 min, 12.5% | 112.8 | 6.0 |
| Comparative example 1 | 0 | — | 120.0 | 0.0 |
| Comparative example 3 | 25 | immediately | 115.2 | 4.0 |

[1]The relative amount based on the total amounts of reaction products in the liquid phase in the reactor Referring to Tables 1 and 2 above, it can be found that Comparative example 1, in which the liquid phase stream through the liquid phase outlet line was not used, took a considerably long time to reach the targeted content of 2-ethyl hexanol compared to Examples 1 to 6, in which the liquid phase stream through the liquid phase outlet line was used for the gas-liquid separation.

In addition, it can be found that in Comparative examples 2 and 3, in which the liquid phase stream was flowed into the gas-liquid separation column from the starting time point of the gas-liquid separation without the control of the separation time point, there was little shortening of the separation time to such an extent that the effect of increasing the efficiency of gas-liquid separation by the liquid phase stream was almost not obtained. From this it can be found that it is important to control the time point when the liquid phase stream flows into the gas-liquid separation column for the increase in the efficiency of the separation process through the liquid phase stream.

Furthermore, it was found that in Examples 4 to 6, the time required to reach the target content of 2-ethyl hexanol was shortened even though the utilization of the liquid phase stream through the liquid phase outlet line was only ¼ as compared to Comparative example 2 and 2-ethyl hexanol could be reduced to a low content even within a short time.

Description of Reference Numerals

11: Esterification reactor
111: Gas phase outlet line
113: Liquid phase outlet line
122: Upper outflow line
12: Gas-liquid separation column
112: Product line
121: Lower recovery line

The invention claimed is:
1. A monohydric alcohol removal method in esterification, the method comprising steps of:
  reacting a carbonyl-based compound having one or more functional groups selected from the group consisting of carboxyl, ester, and acid anhydride groups with a monohydric alcohol in an esterification reactor, wherein the esterification reactor comprises:
    a reaction space having a liquid phase section and a gas phase section;
    a gas phase outlet line located at the upper part of the reaction space and connected to the gas phase section in the reactor; and
    a liquid phase outlet line located at the side part of the reaction space and connected to the liquid phase section in the reactor; and
  separating a gas phase stream containing the monohydric alcohol from the gas phase outlet line in a gas-liquid separation column, wherein separating the gas phase stream comprises removing the monohydric alcohol from the gas phase stream; and separating a liquid phase stream containing the monohydric alcohol from the liquid phase outlet line in the gas-liquid separation column, wherein separating the liquid phase stream comprises removing the monohydric alcohol from the liquid phase stream, wherein an inflow of the liquid phase stream into the gas-liquid separation column starts at a time point between 10% and 70% of a total time required for the gas-liquid separation.

2. The method of claim 1, wherein the inflow of the liquid phase stream into the gas-liquid separation column starts at the time point between 35% and 65% of the total time required for the gas-liquid separation.

3. The method of claim 1, wherein the inflow of the liquid phase stream into the gas-liquid separation column starts at the time point between 45% and 58% of the total time required for the gas-liquid separation.

4. The method of claim 1, wherein the gas phase stream flows out to the gas phase outlet line by reduction in the pressure of the esterification reactor.

5. The method of claim 1, wherein the gas-liquid separation column is a tray type, a packed type, or a mixed type thereof.

6. The method of claim 1, further comprising a step of additionally putting alcohol for trans-esterification into the esterification reactor so as to perform trans-esterification after the monohydric alcohol removal step, wherein the esterification is direct esterification, and wherein the carbonyl-based compound has two or more functional groups selected from the group consisting of carboxyl, ester, and acid anhydride groups.

7. The method of claim 6, wherein the alcohol for trans-esterification has a different alkyl group from an alkyl group of the monohydric alcohol applied directly into the esterification.

* * * * *